United States Patent [19]

Andersson et al.

[11] Patent Number: 4,655,710

[45] Date of Patent: Apr. 7, 1987

[54] METHOD FOR REPLACING LOST DENTAL SUBSTANCE

[76] Inventors: Knut M. G. Andersson, S-830 20 Fåker; Karl E. M. Andersson, S-834 00 Brunflo, both of Sweden

[21] Appl. No.: 675,083

[22] Filed: Nov. 26, 1984

[30] Foreign Application Priority Data

Jan. 26, 1984 [SE] Sweden .................................. 8400396

[51] Int. Cl.⁴ ............................................... A61C 5/10
[52] U.S. Cl. ....................................... 433/223; 433/218
[58] Field of Search ................ 433/223, 200, 222, 229, 433/215, 167, 218, 76; 219/69 E, 69 M

[56] References Cited

U.S. PATENT DOCUMENTS 4,363,627 12/1982 Windeler ............................. 433/223
4,411,626 10/1983 Becker et al. ....................... 433/223
4,478,580 10/1984 Barrut ................................. 433/223

Primary Examiner—John J. Wilson
Attorney, Agent, or Firm—Hammond & Littell, Weissenberger & Dippert

[57] ABSTRACT

The present invention relates to a method for replacing lost tooth substance wherein a model is made from an impression of a prepared tooth or teeth upon which the replacement is to be made. The model serves as a master for transferring the shape of the model to work pieces by means of mechanical processing means.

11 Claims, 6 Drawing Figures

METHOD FOR REPLACING LOST DENTAL SUBSTANCE

The present invention relates to a method for replacing lost tooth substance, and particularly to a method for forming so-called permanent prostheses (permanent replacements) i.e., false teeth which cannot be removed from the mouth without damaging or destroying the prostheses. In every day language, such teeth are referred to as crowns in the case of a single tooth and bridges in the case of a number of mutually adjacent teeth.

BACKGROUND ART

In orthodontology, the most normal method used when replacing lost or decayed tooth substance in a single tooth, or when replacing teeth which have been lost for some reason or other, is one in which the replacement substance or material is cast or molded in an alloy of gold. In the former case, the lost tooth substance is replaced with a gold insert (minor losses of tooth substance), while in the latter case, the replacement is in the form of a crown prosthesis which may be of varying design, such as full crowns and partial crowns. Full crowns may be made entirely of metal. As the name implies, the partial crowns only replace a part of the crowns of the teeth. Both full crowns and partial crowns are designed to include the remaining parts of the tooth crown or crowns. Separate gold fillings and individual crown prostheses, and also bridge prostheses, are called permanent fixtures or replacements since they are normally cemented to the teeth and cannot be removed without being broken.

Before a tooth can be filled with gold or fitted with a crown prosthesis, it must first be shaped and prepared. Existing guidelines and rules relating to the preparatory work involved are well known to those skilled in this art and do not constitute any part of the present invention. Consequently, they will not be dealt with in detail here. When dental gold work is cast or moulded, there is first always formed a wax model of the teeth being repaired, which is then embedded in a mould and the wax is subsequently replaced with a gold alloy. The wax model is most often produced by the so-called indirect method, by which is meant that all, or the greater part, of the dental work involved is carried out on a mould, i.e., an impression of the relevant part of the oral cavity. Such a model, referred to as the preparation model, is often not sufficient in itself to enable dental gold work to be carried out, since it must also be capable of being placed, in one way or another, in correct relationship with surrounding and corresponding parts of the bite. Consequently, a working model incorporating the copy of the prepared teeth is normally produced.

The actual casting process, as applied today, incorporates a number of working stages comprising the following (a) forming in the wax a runner through which the casting metal can be poured, or fixing a metal runner to the wax model;

(b) embedding the wax model together with the runner in a heat-resistant bedding mass;

(c) heating the embedding mass to eliminate the wax and runner therefrom;

(d) permitting the molten metal to fill the mould freed from wax, via mould craters and runners; and (e) working the solidified metal, for example, grinding and polishing the same and applying surface material to the thus worked surfaces.

It will be evident herefrom that the work involved in replacing lost tooth substance is extremely complicated. It is also a known fact to those skilled in this art that the casting process places high demands on the expertise and accuracy of the person carrying out the work.

Different types of cast gold constructions place different requirements on the hardness and mechanical strength of the gold alloy used. For example, while a buccal gold filling, which is subject to no load or only an insignificant load, can be cast advantageously from a soft alloy, the alloy used to build a bridge, a crown or a filling subjected to heavy pressure by the teeth must be much harder and of much greater mechanical strength. The chewing habits and abrasion tendencies of the patient are two factors which influence the choice of the casting alloy.

In recent years the use of hard-gold alloys has progressively increased, the mechanical and electrochemical properties of these alloys being improved by admixing metals from the platinum metal group.

Irrespective of the alloy used, its gold content is normally at least 70%. In recent time, however, doubt has been expressed as to whether, from a biological aspect, gold can be considered an acceptable material in this respect. It has also been found that copper, palladium etc., are precipitated, which can result in subsidiary effects, at least in the long term.

Furthermore, gold is, in itself, a very expensive metal which together with the relatively complicated casting process required renders the total cost for an insert, filling, crown or the like highly expensive.

DISCLOSURE OF THE INVENTION

Consequently, there are many factors, i.e., economical, technical and biological, which call for the introduction of a completely novel manufacturing technique with respect to the production of replacements for lost tooth substance, and accordingly the object of the present invention is to provide one such novel method. The invention also relates to means for carrying out the novel method.

The novel method according to the present invention is characterized in that the model, which in a known manner incorporates both the prepared tooth and the detachable sleeve which is placed over the prepared tooth and which forms a prototype of the visible tooth replacement, forms in a first working phase a master from which the outer form of the master sleeve is transferred to a first workpiece by mechanical processing; in that in a second working phase the model forms a master for transferring the form of the prepared tooth to a second workpiece by mechanical processing; and in that the outer form of said second workpiece is transferred to the interior of the first workpiece by mechanical processing.

The advantages afforded by this method will readily be understood. Although the replacement material may be castable or mouldable, it need not necessarily be so. The element titanium suggested for use as a replacement material by way of example, is biologically acceptable and satisfies all other demands placed on such replacement material, such as abrasion resistance. At present day prices, titanium is much cheaper than gold. As proposed in claim 2, an advantage is gained when the first working phase is followed by a step in which the exact relationship between the outer and inner configurations of the tooth replacement is obtained, this being effected, for example, by fixing the outer form of the tooth replacement in a holder and thereafter separating the outer form of the tooth replacement from the remainder of the workpiece. This fixed position is the utilized, by allowing work on the interior of the first work piece to be commenced upon completion of the second working phase.

In its simplest form, the novel method according to the invention can be carried out with the aid of a conventional templet miller and an electro-erosive machine. As will be understood by those skilled in this art, special working machines can be constructed for this purpose, the functions of which correspond to the functions of the aforesaid types of machine.

Fixation of the workpiece positions enabling the end product to be given a precisely, fitting shape, can be effected by means of known electrode holders, for example, holders of the kind designated SYSTEM 3R ®.

An embodiment of the invention will now be described by way of example with reference to the accompanying drawing, in which the novel method is explained step by step.

TECHNICAL DESCRIPTION

Figure 1:
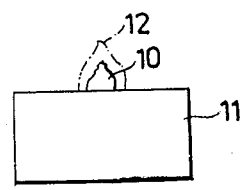
FIGS. 1 to 6 represent planar views of apparati useful according to an embodiment of the invention.

FIG. 1 illustrates a model of the tooth residue 10 upon which the dentist has worked and which is intended to form an anchorage for a tooth replacement, i.e., a false or artificial tooth. The model is produced from a conentional impression taken from the mouth of a patient, and is normally made by a dental technician. The model may be made of gypsum, plastic or some other material, and the tooth residue is caused to project above the upper surface of a holder 11. In a similar manner there is prepared a sleeve-like part 12, suitably from a plastic material, which is fitted over the tooth residue. These two working steps coincide with the known technique set forth in the preamble of the present application.

The novel method according to the invention, and the preferred means for carrying out the method, are schematically illustrated in FIGS. 2-7 and described hereinafter with reference to these figures.

Figure 2:
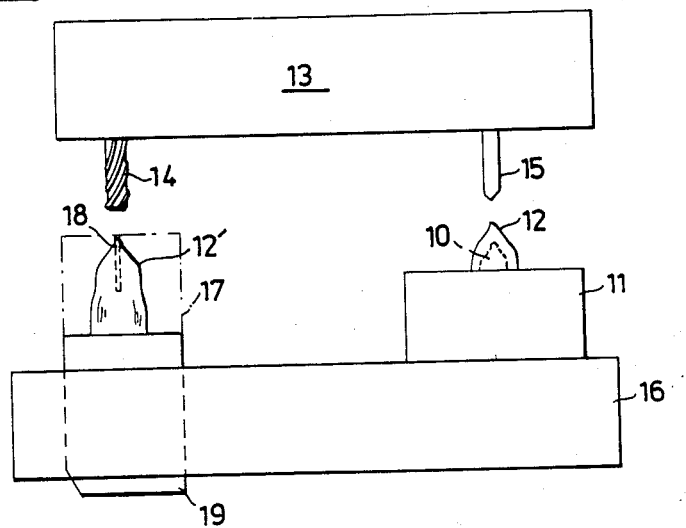

In FIG. 2 the reference 13 identifies the working head of a mechanical tool, for example, a conventional templet miller provided with a working tool 14 and a follower 15. The function and working mode of a templet miller is presumed to be known and will not therefore be described in detail. The finished model of a tooth 10, 11, 12 (shown in FIG. 1) is placed on a horizontal platen 16 located vertically beneath the follower 15, the platen being provided with means for fixing the position of the tooth model thereon. The model 10, 11, 12 is fixed in position on the platen 16 so that no undercut occurs during the mechanical working of the model, as described hereinafter. Secured in position approximately vertically beneath the rotatable tool 14 is a suitable, homogeneous workpiece 17, which is preferably made of titanium or some titanium alloy, or some other suitable, preferably non-castable material. The workpiece 17 may initially have any shape whatsoever, although it is important that the dimensions of the workpiece 17 are greater than the dimensions of the model 10, 11, 12. In the illustrated embodiment, there is arranged in the upper free end of the workpiece 17, a bore 18, for accommodating cooling liquid during the working process.

The workpiece 17 is removably fixed in position in a holder 19, for example, an electrode holder of the kind sold under the name SYSTEM 3R. The holder 19 is removably fixed to the table 16. The upper part 12' of the workpiece is now mechanically worked and brought to a shape which corresponds precisely to the outer contours of the sleeve or jacket 12 in FIGS. 1 and 2, these outer contours being shown in full lines in FIG. 2, and the model 10, 11, 12 can now serve as a master.

Upon completion of this working procedure, the holder 19 and the workpiece 17 are removed as a unit from the table 16, the set position of the workpiece 17 being retained during this working process.

Figure 3:
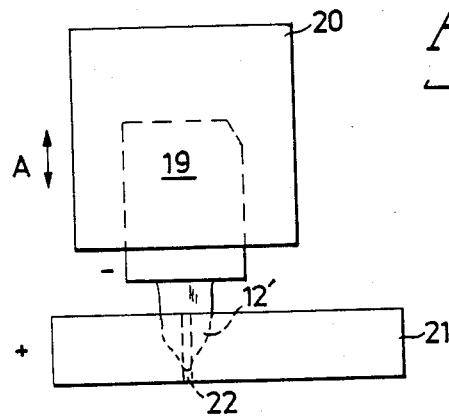

The next phase of the novel method is illustrated in FIG. 3. In this phase, the holder 19 and the mechanically worked workpiece 17 illustrated in FIG. 2 is transferred as an integral unit from a preceding working phase to a conventional electroarcing machine 20, which operates vertically in the direction of the arrow A in a conventional manner. The mechanically worked workpiece 17 made of titanium, for example is faced downwardly towards a plate 21 which is preferably made of brass and has a predetermined thickness and which is detachably mounted on the platen (not shown) of the electroarcing machine. In the illustrated embodiment, the plate 21 is provided with a through-passing hole 22 of suitable diameter, through which a cooling liquid can be passed during the working process. The working range of the electroarcing machine 20 in the vertical direction is predetermined by a stop means arranged on the machine. The working depth in the plate 21 is determined by the form or configuration 12'. In this way, the brass plate 21 electrically forms the positive pole while the workpiece 17 serves as the electrode and thus forms the negative pole. Such electroarcing work processes are well known and require no further explanation. Consequently, the free end of the workpiece 17 machines the plate 21 in a known manner, such that the plate is subsequently imparted an internal configuration which corresponds exactly to the configuration of the free end 12' of the workpiece 17, thus the outer configuration or contours of the visible part of the replacement to be produced, the purpose of this working phase being to determine precisely the relationship between the internal and external configurations of the tooth replacement.

Figure 4:
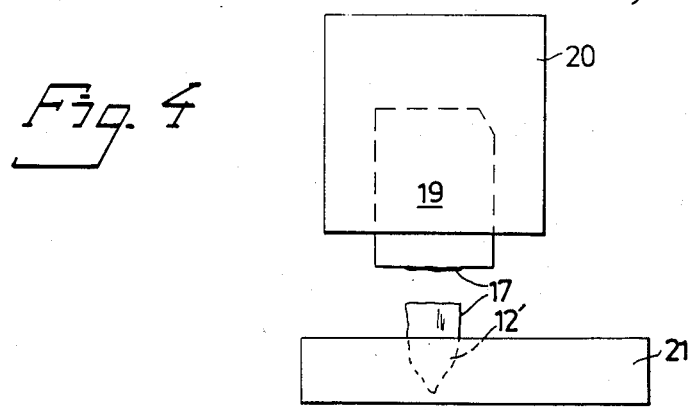

In FIG. 4 the workpiece 17 is shown to be truncated in a known manner, to form a workpiece 17' which still co-acts with the plate 21 and which has not been disturbed from the position it occupied in the working phase of FIG. 3.

Figure 5:
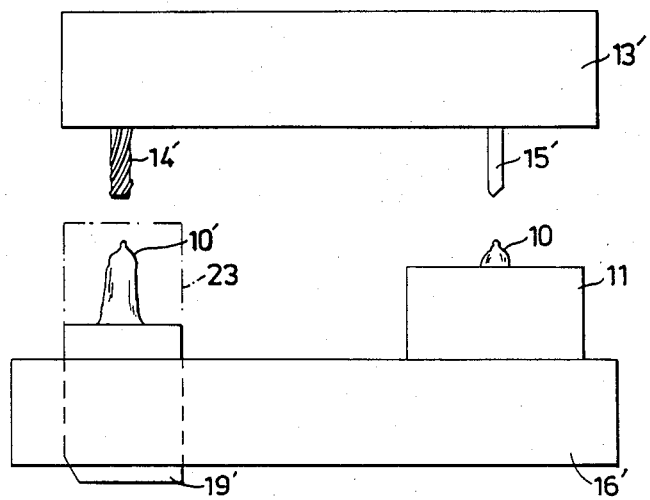

In the next following working phase schematically illustrated in FIG. 5, there is used a machining tool 13', preferably of the same kind as that illustrated in FIG. 2, thus a templet miller, the movable working head of which carries a milling tool 14' and a follower 15'.

An electrode holder 19' of the kind illustrated in FIG. 5 is detachably connected to a workpiece 23 on which work is to be carried out. This workpiece may be made of any suitable material. Carbon is one such material which satisfactorily fulfils all requirements in this respect. As with the arrangement illustrated in FIG. 2, the electrode holder 19' and its workpiece 23 are arranged vertically beneath the milling tool 14' on a platen 16'.

The model 10, 11 is arranged vertically beneath the follower 15', although the sleeve 12 is removed in this case. The model 10,11 also serves here as a master, and the workpiece 23 is mechanically worked to obtain, by means of the follower 15' an exact replica 10' of the tooth residue 10 of the model. The electrode 19' and the workpiece 23 shaped to the replica 10' are then moved in the form of a unit in the next following phase (FIG. 6) to an electroarcing machine, preferably of the kind described with reference to FIG. 3. The brass plate 21 with the previously worked workpiece 17' is fixedly positioned on the platen (not shown) of the electroarcing machine 20 beneath the working head. In this case, the workpiece 23 serves as the electrode and thus the negative pole, while the plate 21 serves as a positive pole, similar to that described with reference to FIG. 3. The workpiece 23 is lowered and machines the workpiece 17' from above, down to a given depth corresponding to the working depth employed in the working phase illustrated in FIG. 3. Upon completion of this working phase, the interior of the workpiece 17', which is preferably made of titanium or a titanium alloy, has been given a shape which corresponds exactly to the configuration of the tooth residue 10, and as a result of the aforesaid positional fixation there is obtained a precise and desired positional relationship between the external and internal configuration of the tooth replacement.

As a result of the aforedescribed mechanical working processes, the workpiece 17' has been given an external shape and an internal, jacket-like appearance such as to provide an artificial tooth replacement totally acceptable with regard to form.

Subsequent to optionally providing a smooth finish on the artificial tooth, all that remains is to provide the tooth with a suitable surface layer. It has been found that an artificial tooth produced in the aforedescribed manner can be inserted into the mouth of a patient without requiring any corrections to the tooth whatsoever, this being made possible initially by determining the position of the workpiece 17 in the working phase illustrated in FIG. 2 (formed by the outer contours of the sleeve) and the following working phase described with reference to FIG. 3, in which the workpiece 17 is fixedly positioned on the plate 21, and the internal machining of the workpiece in accordance with FIG. 6.

Although the illustrated embodiment employs the use of known machine tools, it will be understood that special machines and tools having the same or equivalent working functions and operational modes may be designed specifically for this purpose.

Figure 6:
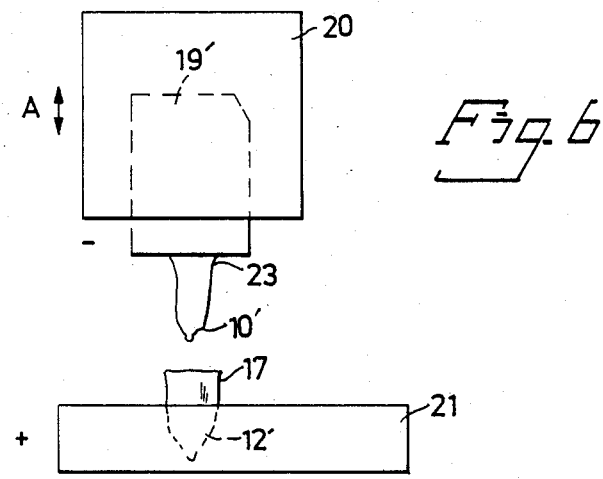

Thus, a number of modifications are conceivable within the scope of the invention with respect to the machines used and the type of electrodes used (particularly the electrode used in the working phase described with reference to FIG. 6).

It will also be understood that the model serving as the master may be different to that described in connection with the illustrated embodiment. For example, the model may comprise available data technology incorporated in the memory store of a copying machine, or paritograph, such date information herewith serving as a master.

Other modifications are also conceivable within the scope of the claims.

We claim:

1. A method of fabricating a dental prosthesis comprising the steps of:
    (a) forming a first replica of residual tooth substance to be repaired;
    (b) fixedly positioning said first replica to project above the upper surface of a first holding means;
    (c) forming a sleeve-like member covering the outer surface of the portion of said first replica projecting above the upper surface of a first holding means, said sleeve-like member having outer surface contours coinciding with the outer contours of desired tooth replacement;
    (d) mechanically copying the outer contours of said sleeve-like member onto a first workpiece removably positioned in a second holding means to form a second replica;
    (e) inserting said second replica into a second workpiece to obtain a fixture holding said second replica at a given position therewith;
    (f) severing said second replica at a point above the surface of said second workpiece;
    (g) removing said sleeve-like member from said first replica;
    (h) mechanically copying the outer contours of said first replica onto a third workpiece to form a third replica;
    (i) mechanically forming in said second replica with the use of said third replica a cavity having contours corresponding to the outer contours of said third replica; and
    (j) removing the thus cavitated second replica from said first workpiece to provide said dental prosthesis.

2. The method of claim 1, wherein said first replica is prepared from a cast impression of residual tooth substance being repaired.

3. The method of claim 1, wherein said first replica is gypsum or a plastic material.

4. The method of claim 1, wherein said sleeve-like member is a plastic material.

5. The method of claim 1, wherein in step (d) the outer contours of said sleeve-like member are mechanically copied by use of a templet miller.

6. The method of claim 1, wherein in step (e) an electroarcing machine is used to position said second replica into said second workpiece.

7. The method of claim 1, wherein in step (h) the outer contours of said first replica are mechanically copied by use of a templet miller.

8. The method of claim 1, wherein in step (i) an electroarcing machine is used to form said cavity.

9. The method of claim 1, wherein said first workpiece is comprised of titanium.

10. The method of claim 1, wherein said second workpiece is comprised of brass.

11. The method of claim 1, wherein said third workpiece is comprised of carbon.

* * * * *